United States Patent
Neuba et al.

(10) Patent No.: US 9,925,133 B2
(45) Date of Patent: *Mar. 27, 2018

(54) MULTI-TONAL ONE STEP DYEING WITH THICKENED PRE-TREATMENT SOLUTION

(71) Applicant: Henkel AG & Co. KGaA, Duesseldorf (DE)

(72) Inventors: Constanze Neuba, Grevenbroich (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,180

(22) Filed: Feb. 16, 2017

(65) Prior Publication Data

US 2017/0157024 A1 Jun. 8, 2017

Related U.S. Application Data

(63) Continuation of application No. PCT/EP2015/068564, filed on Aug. 12, 2015.

(30) Foreign Application Priority Data

Aug. 26, 2014 (DE) .................. 10 2014 216 943

(51) Int. Cl.

| | | |
|---|---|---|
| *A61Q 5/10* | (2006.01) | |
| *A61K 8/81* | (2006.01) | |
| *A61K 8/22* | (2006.01) | |
| *A61K 8/49* | (2006.01) | |
| *A61K 8/42* | (2006.01) | |
| *A61K 8/23* | (2006.01) | |
| *A61K 8/20* | (2006.01) | |
| *A61K 8/19* | (2006.01) | |
| *A61K 8/73* | (2006.01) | |
| *A61K 8/41* | (2006.01) | |

(52) U.S. Cl.
CPC .............. *A61K 8/8182* (2013.01); *A61K 8/19* (2013.01); *A61K 8/20* (2013.01); *A61K 8/22* (2013.01); *A61K 8/23* (2013.01); *A61K 8/411* (2013.01); *A61K 8/415* (2013.01); *A61K 8/42* (2013.01); *A61K 8/4966* (2013.01); *A61K 8/73* (2013.01); *A61K 8/731* (2013.01); *A61K 8/8147* (2013.01); *A61K 8/8152* (2013.01); *A61K 8/8158* (2013.01); *A61Q 5/10* (2013.01); *A61K 2800/4324* (2013.01)

(58) Field of Classification Search
CPC ...... A61K 8/8182; A61K 8/22; A61K 8/4966; A61K 8/42; A61K 8/23; A61K 8/20; A61K 8/19; A61K 8/731; A61K 8/8147; A61K 8/8158; A61K 8/8152; A61K 8/73; A61K 8/415; A61K 8/411; A61K 2800/4324; A61Q 5/10

See application file for complete search history.

(56) References Cited

U.S. PATENT DOCUMENTS

| | | | |
|---|---|---|---|
| 5,431,698 A * | 7/1995 | Tennigkeit | A61K 8/411 8/406 |
| 6,916,343 B1 * | 7/2005 | Akram | A61K 8/418 8/405 |
| 9,402,795 B2 * | 8/2016 | Neuba | A61Q 5/10 |
| 9,445,977 B2 * | 9/2016 | Neuba | A61K 8/411 |
| 2005/0000035 A1 * | 1/2005 | Chan | A61K 8/22 8/405 |

FOREIGN PATENT DOCUMENTS

DE   10 2014 216 943.7   *   8/2014

OTHER PUBLICATIONS

PCT International Search Report (PCT/EP2015/068564) dated Jul. 9, 2015.

* cited by examiner

*Primary Examiner* — Eisa B Elhilo
(74) *Attorney, Agent, or Firm* — David K. Benson

(57) ABSTRACT

A method for dyeing keratinous fibers, in particular, human hair, in which, after a thickened pre-treatment agent (M1) containing no oxidation dye precursors has been applied and allowed to react, a coloring agent (M2) is applied and allowed to react immediately thereafter and without rinsing. By carrying out said method, hair can be colored in a dyeing step and simultaneously multi-tonal dyeing with highlights or lowlights can be achieved.

17 Claims, No Drawings

US 9,925,133 B2

MULTI-TONAL ONE STEP DYEING WITH THICKENED PRE-TREATMENT SOLUTION

FIELD OF THE INVENTION

The present invention generally relates to a method for treating keratinous fibers, which makes it possible to color the hair in one dyeing step and simultaneously achieve multi-tonal dyeing with highlights or lowlights in small strands.

BACKGROUND OF THE INVENTION

Over time and particularly with exposure to external influences such as light or harmful atmospheric pollutants, hair loses or changes its natural color and its shine or luster. For this reason, hair coloring agents are widely used either at hair salons or at home.

For permanent, intense colorations having appropriate fastness properties, so-called oxidation dyes are used. Such coloring agents customarily include oxidation dye precursors, so-called developer components and coupler components, which form the actual dyes with one another under the influence of oxidizing agents or atmospheric oxygen. Oxidation dyes are characterized by excellent, long-lasting dyeing results. Coloring or tinting agents containing so-called substantive dyes ("direct dyes") as the coloring component are typically used for temporary colors.

Apart from dyeing, the lightening of the natural hair color or dyeing the hair a blond color is the very specific wish of many consumers, because a blond hair color is regarded as attractive and fashionably desirable. If substrates are to be lightened or even bleached, the dyes coloring the substrate are most often oxidatively decolorized with the use of appropriate oxidizing agents, such as hydrogen peroxide.

In hair dyeing, particularly in hair dyeing at home, a problem arises in that natural color shades are completely covered, so that multi-tonal colors are difficult to realize.

Partially decolorizing dyed hair by the selective use of oxidizing agents to give the hair a more natural appearance is known in the prior art. Hair sections ("small strands") to which the oxidizing agents are applied thereby bleach out at least partially, resulting in a multi-tonal hair color. The oxidizing agent is applied then with a brush or applicator, wherein hair not to be treated is protected from decolorizing optionally by aluminum foil or a so-called "highlighting cap."

This type of application does in fact solve the problem of the most natural possible dyeing of hair, but allows only the placing of "highlights." Achieving "lowlights," i.e., darker sections, necessitates dyeing the hair again. In each of the cases, a time-consuming second decolorizing or dyeing step that follows the original dyeing is therefore necessary. In particular in use at home, therefore, the entire hair must first be colored before the consumer can place "highlights" or "lowlights." Many consumers regard this as time-consuming and also frustrating, because the essential color-changing step occurs at the beginning and is only "corrected" in a second step.

It is therefore desirable to provide a method that makes multi-tonal dyeing in one dyeing step possible. Then, the dyeing of the hair should accompany the generation of "highlights" or "lowlights", so that a result is visible immediately after the coloring agent is rinsed out.

Furthermore, other desirable features and characteristics of the present invention will become apparent from the subsequent detailed description of the invention and the appended claims, taken in conjunction with this background of the invention.

BRIEF SUMMARY OF THE INVENTION

A method for oxidatively dyeing keratinous fibers includes the following method steps in the specified order: a) applying a cosmetic agent (M1) to the keratinous fibers; b) allowing the agent (M1) to act on the keratinous fibers for a period of time of 30 seconds to 40 minutes; c) applying a cosmetic agent (M2) to the keratinous fibers exposed to the cosmetic agent (M1); d) allowing the cosmetic agents (M1) and (M2) to act on the keratinous fibers for a period of time of 1 to 70 minutes; and e) rinsing out the cosmetic agents (M1) and (M2), characterized in that the cosmetic agent (M1) includes at least one direct dye (M1-1), and includes at least one thickening agent (M1-2), and includes no oxidation dye precursors (M1-3); and the cosmetic agent (M2) includes at least one oxidation dye precursor (M2-1), and at least one oxidizing agent (M2-2).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that partially pre-treating fiber areas or small strands results in these areas or small strands being more intensively or less intensively dyed later. Pre-penetrating or pre-treating individual fiber areas or small strands causes the coloring agent that is used immediately thereafter to multi-tonally color the hair and yields a natural dyeing result with "highlights" or lowlights" immediately after the dyeing step.

A subject matter of the present invention is a method for oxidatively dyeing keratinous fibers, wherein the method comprises the following method steps in the specified order:
  a) applying a cosmetic agent (M1) to the keratinous fibers,
  b) allowing the agent (M1) to act on the keratinous fibers for a period of time of 30 seconds to 30 minutes,
  c) applying a cosmetic agent (M2) to the keratinous fibers exposed to the cosmetic agent (M1),
  d) allowing the cosmetic agents (M1) and (M2) to act on the keratinous fibers for a period of time of 1 to 70 minutes, and
  e) rinsing out the cosmetic agents (M1) and (M2), characterized in that
  the cosmetic agent (M1) includes at least one direct dye (M1-1) and at least one thickening agent (M1-2), and includes no oxidation dye precursors (M1-3); and
  the cosmetic agent (M2) includes at least one oxidation dye precursor (M2-1), and at least one oxidizing agent (M2-2).

The term "keratinous fibers or even keratin fibers" is understood according to the present invention to mean fur, wool, feathers, and human hair. Within the framework of the present invention, it is especially preferable when the method according to the present invention is used to dye human hair.

Furthermore, the term "thickening agent" is understood within the framework of the present invention to mean compounds that can bind liquids, especially water, and increase the viscosity of these liquids. This, within the framework of the present invention, also includes gelling agents, which are able to thicken liquids into compositions with a gel-like consistency or into gels. Gel-like cosmetic agents or gels are understood, according to the present invention, to mean dimensionally stable, easily deformable dispersed systems made of at least two components—the gelling agent (most often a solid, colloidally-dispersed having long or heavily branched compounds) and a liquid (most often water) as a dispersant. The gelling agent creates a spatial network within the liquid, wherein the individual gel-forming compounds adhere to one another due to primary and/or secondary valencies at different spatial points.

Preferably according to the present invention, the method steps a) to e) are carried out in the aforementioned order with a time interval between the individual method steps of 0 to 60 minutes, each, preferably 0 to 40 minutes each, in particular, 0 to 30 minutes.

In the first method step (method step a)) of the method according to the present invention, a cosmetic agent (M1) is applied to the fibers. This cosmetic agent (M1), referred to hereinbelow also as a pre-treatment agent or a pre-penetration agent, is left on the keratinous fibers for a period of time of 30 seconds to 30 minutes (step b) of the method according to the present invention).

However, rather shorter exposure times for the pre-treatment agent are preferable according to the present invention. Especially preferable methods according to the present invention are characterized in that the cosmetic agent (M1) is allowed to act on the keratinous fibers in the method step b) for a duration of 30 seconds to 30 minutes, preferably 30 seconds to 20 minutes, preferably 30 seconds to 18 minutes, in particular, 30 seconds to 15 minutes. Pre-treating keratinous fibers with the cosmetic agent (M1) leads to the ingredients of the pre-treatment agent (M1) adhering at these places to the keratinous fibers or penetrating into the keratinous fibers, so that the dyeing result is reinforced or brightened when the cosmetic agent (M2) is subsequently applied to these places. In this manner, hair can be colored in a dyeing step and simultaneously multi-tonal dyeing with highlights or lowlights in small strands can be achieved.

It has been shown that a pre-treatment at slightly elevated temperatures renders the multi-tonal effect even more vivid. Methods that are preferred according to the present invention are characterized in that the cosmetic agent (M1) is allowed to act in method step b) at a temperature of 20° C. to 120° C., in particular, 30° C. to 120° C. Temperatures of 30° C. to 120° C., preferably 40° C. to 120° C., can be achieved, for example, with the use of a hot air blower or a drying hood.

In order for multi-tonal colorations to be achieved, the cosmetic agent (M1) is not to be applied evenly onto the keratinous fibers. Preferably, the cosmetic agent (M1) is applied only to individual regions, especially preferably, only to individual small strands. Alternatively, the concentration of the cosmetic agent (M1) applied to the individual small strands may be varied. It is also possible to at first evenly apply the cosmetic agent (M1) to all of the keratinous fibers, and then treat individual regions or small strands again with the cosmetic agent (M1). Repeatedly treating individual regions/small strands with the cosmetic agent (M1) is also possible according to the present invention.

In this context, it is especially preferable when the cosmetic agent (M1) is applied only to individual small strands in method step a). The term "small strands" is understood according to the present invention to mean a part that is separated from the entirety of keratinous fibers and is composed of at least two, preferably at least 50, in particular, at least 100 keratinous fibers.

After the exposure time for the pre-treatment agent, the keratinous fibers are not rinsed or wiped off. Rather, in method step c) of the method according to the present invention, a cosmetic agent (M2) is applied onto the keratinous fibers, which are still being exposed to the cosmetic agent (M1). The mixing of the cosmetic agents (M1) and (M2) resulting from the application of the cosmetic agent (M2) onto the keratinous fibers is allowed to act for a duration of 1 to 70 minutes in method step d) of the method according to the present invention.

According to the present invention, however, rather shorter exposure times for the cosmetic agents (M1) and (M2) in method step d) are preferred. Especially preferable methods according to the present invention are characterized in that the cosmetic agents (M1) and (M2) are allowed to act for a duration of 1 to 60 minutes, preferably 5 to 50 minutes, in particular, 10 to 45 minutes in method step d).

Because the cosmetic agent (M1) has already been left on the keratinous fibers for a certain length of time in method step b) of the method according to the present invention, these keratinous fibers are in contact with the contents of the cosmetic agent (M1) for a longer period of time than with those of the cosmetic agent (M2). If the cosmetic agent (M1) has been used only on individual small strands or in individual regions, the contents of the cosmetic agent (M1) are able to act more intensively in these regions and thus intensify or lessen the action of the contents of the cosmetic agent (M2) in these regions, whereby a darker or lighter dyeing of these regions is achieved.

After the cosmetic agents (M1) and (M2) have been rinsed out in method step e) of the method according to the present invention, a multi-tonal color result is obtained immediately, without the need to perform any additional steps.

The cosmetic agent (M1)/pre-treatment agent entails a hair dye that includes at least one direct dye (M1-1). Direct dyes are dyes that are taken directly up into the hair and do not require an oxidative process to form the color. Direct dyes are typically nitrophenylenediamines, nitroaminophenols, azo dyes, anthraquinones, or indophenols.

According to a preferred embodiment of the subject matter of the present invention, the at least one direct dye (M1-1) is selected from the group consisting of anionic direct dyes, cationic direct dyes, nonionic direct dyes, and mixtures thereof In this context, it may be provided, according to the present invention, that the anionic direct dye is selected from the group consisting of Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Tetrabromophenol Blue, and/or physiologically acceptable salts thereof Within the framework of this embodiment, it may furthermore be provided that the cationic direct dye is selected from the group consisting of Basic Blue 7, Basic Blue 26, Basic Violet 2 and Basic Violet 14, Basic Yellow 57, Basic Red 76, Basic Blue 99, Basic Brown 16 and Basic Brown 17 and HC Blue 16, as well as Basic Yellow 87, Basic Orange 31 and Basic Red 51, and/or physiologically acceptable salts thereof. It may moreover be provided, within the framework of this embodiment, that the nonionic direct dye is selected from the group consisting of HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 1 1, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)amino-2-nitrobenzene, 3-nitro-4-(2-hydroxyethyl) aminophenol, 2-(2'-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid, 2-amino-6-chloro-4-nitrophenol, 4-ethylamino-3-nitrobenzoic acid and 2-chloro-6-ethylamino-4-nitrophenol, and/or physiologically acceptable salts thereof, preferably 2-amino-6-chloro-4-nitrophenol and/or 4-amino-3-nitrophenol and/or physiologically acceptable salts thereof.

Pre-treatment agents (M1) that are especially preferably used within the framework of the method according to the present invention contain at least one direct dye (M1-1) selected from the group consisting of 2-amino-6-chloro-4-nitrophenol, HC Blue 12, HC Yellow 2, HC Violet 14D, and/or physiologically acceptable salts thereof and mixtures thereof. When these specific direct dyes are used, an especially balanced and subtle shades can be formed during the method according to the present invention or in the multitonal dyeing.

Preferably according to the present invention, the cosmetic agent (M1) includes the at least one direct dye (M1-3) in a total amount of 0.00001 to 5.0 wt %, preferably 0.0001 to 5.5 wt %, preferably 0.0005 to 5.0 wt %, preferably 0.001 to 4.5 wt %, further preferably 0.001 to 4.0 wt %, in particular, 0.001 to 3.0 wt %, relative to the total weight of the cosmetic agent (M1). The aforementioned amounts of the direct dye lead to especially balanced shades in the framework of the multi-tonal dyeing according to the method according to the present invention.

In order to set the desired viscosity and prevent the cosmetic agent (M1) from flowing down during the application to the keratinous fibers and during the exposure time in method step b), the cosmetic agents (M1) contain at least one thickening agent (M1-2).

According to a preferred embodiment of the subject matter of the present invention, the at least one thickening agent (M1-2) is selected from the group consisting of thickening polysaccharides, thickening synthetic polymers, thickening inorganic compounds, and mixtures thereof.

In this context, it may be provided, according to the present invention, that the thickening polysaccharide is selected from the group consisting of xanthan, celluloses, cellulosic derivatives, curdlan, algins, alginates, glucans, pullulans, amyloses, tragacanth, karaya gum, ghatti gum, agar, carrageenan, chitin, chitosan, gum arabic, gellan, guar gum, locust bean gum, and mixtures thereof, preferably xanthan, celluloses, cellulosic derivatives, and mixtures thereof.

Within the framework of this embodiment, it may furthermore be provided that the thickening synthetic polymer is selected from the group consisting of: crosslinked homopolymers or copolymers of acrylic acid, methacrylic acid, and salts and alkyl esters thereof; homopolymers or copolymers of acrylamides and/or methacrylamides; copolymers of acrylic acid and acrylamides and mixtures thereof; preferably crosslinked homopolymers or copolymers of acrylic acid, methacrylic acid, and salts and alkyl esters thereof; crosslinked copolymers of ethoxylated alkyl esters of methacrylic acid and sulfonated acrylamides, as well as salts thereof; and crosslinked copolymers of methacrylic acid, acrylamides, sulfonated acrylamides, and salts thereof. Especially preferable is the crosslinked copolymer known under the INCI name Ammonium Acryloyldimethyltaurate/Beheneth-25 methacrylate Crosspolymer, which is commercially available, for example, under the trade name Aristoflex HMB from Clariant. The crosslinked copolymer with the INCI name Acrylates/$C_{10-30}$ Alkyl Acrylate Crosspolymer, which is available under the trade name Carbopol from Lubrizol, is also especially preferable within the framework of this embodiment. The crosslinked copolymer known under the INCI name Polyacrylate Crosspolymer-11, which is commercially available under the trade name Aristoflex Velvet from Clariant, is additionally preferable within the framework of this embodiment.

It may additionally be provided, within the framework of this embodiment, that the thickening anionic compound is selected from the group consisting of: electrolytes, in particular, sodium chloride and potassium chloride; phyllosilicates; magnesium aluminum silicates; optionally modified bentonites, in particular, optionally modified smectites; and mixtures thereof Cosmetic agents (M1) that are especially preferably used within the framework of the method according to the present invention contain at least one thickening agent (M1-2) selected from the group consisting of: celluloses; cellulosic derivatives; xanthan; crosslinked homopolymers or copolymers of acrylic acid, methacrylic acid, and salts thereof; crosslinked copolymers of ethoxylated alkyl esters of methacrylic acid, sulfonated acrylamides, and salts thereof; crosslinked copolymers of methacrylic acid, acrylamides, and sulfonated acrylamides, and salts thereof; and mixtures of these thickening agents. To enable neat and locally-limited application of the pre-penetration agent (M1), a gel-like viscosity of the agent has proven to be advantageous. The gel-like pre-treatment agent (M1) ensures, on the one hand, a favorable and uniform distribution onto the keratinous fibers, but, on the other hand, does not lead to running or flowing out during the exposure time in method step b). In this manner, the pre-treatment agent (M1) can be applied and allowed to act to limited small strands or regions, so as to result in an excellent multi-tonal dyeing result without smearing of the small strands due to running of the pre-treatment agent (M1).

Within the framework of the method according to the present invention, it may furthermore be preferable when two mutually different thickening agents (M1-2) selected from crosslinked homopolymers or copolymers of acrylic acid, methacrylic acid, and salts thereof and xanthan are used in the cosmetic agents (M1).

Preferably according to the present invention, the cosmetic agent (M1) includes the at least one thickening agent (M1-2) in a total amount of 0.1 to 5.0 wt %, preferably 0.3 to 4.5 wt %, preferably 0.5 to 4.0 wt %, further preferably 0.7 to 3.5 wt %, in particular, 0.8 to 3.0 wt %, relative to the total weight of the cosmetic agent (M1). The aforementioned amounts of the thickening agents ensure sufficient thickening, so as to prevent running of the pre-treatment agent (M1) during the exposure time in method step b), and any resulting smearing of the multi-tonal dyeing result. Furthermore, these amounts of thickening agents ensure a favorable and uniform distribution of the pre-treatment agent (M1) onto the keratinous fibers.

According to the present invention, the cosmetic agent (M1) is free of oxidation dye precursors (M1-3). "Oxidation dye precursors" are understood within the framework of the present invention to mean compounds of the developer type and of the coupler type that form the corresponding dyes when exposed to an oxidizing agent, e.g., hydrogen peroxide, in oxidative coupling reactions.

The term "free of" signifies here, within the framework of the present invention, that the cosmetic agents (M1) do not contain any oxidation dye precursors. More concretely, therefore, "free of" signifies that the cosmetic agents (M1) used in method step a) contain less than 1.0 wt %, preferably less than 0.5 wt %, preferably less than 0.25 wt %, further preferably less than 0.1 wt %, in particular, 0.0 wt % oxidation dye precursors, relative to the total weight of the cosmetic agent (M1).

Methods that are preferred according to the present invention are therefore characterized in that the cosmetic agent (M1) used in method step a) includes less than 1.0 wt %, preferably less than 0.5 wt %, preferably less than 0.25 wt %, further preferably less than 0.1 wt %, in particular, 0.0 wt % oxidation dye precursors—in particular, developer components and coupler components—relative to the total weight of the cosmetic agent (M1).

Within the framework of the method according to the present invention, to avoid running of the pre-treatment agent (M1) and thus to avoid smearing of the multi-tonal dyeing result, it is advantageous when the pre-treatment agents (M1) are present in the form of gel-like cosmetic agents. Cosmetic agents (M1) that are preferably used according to the present invention therefore have a dynamic viscosity of 5,000 to 90,000 mPa·s, preferably 6,000 to 80,000 mPa·s, preferably 8,000 to 70,000 mPa·s, further preferably 9,000 to 60,000 mPa·s, in particular, 10,000 to 50,000 mPa.s, in each case as measured with a Brookfield RDV II+, spindle nr. 4, 4 rpm, 20° C.

In addition to the direct dye(s) and the thickening agent (s), the cosmetic agent (M1) used in the method according to the present invention may also contain additional ingredients.

Preferably according to the present invention, the cosmetic agent (M1) additionally includes at least one additional compound selected from the group consisting of (i) surfactants, (ii) glycols, (iii), alkalizing agents, and (iv) mixtures thereof.

Surfactants within the meaning of the present invention are amphiphilic (bifunctional) compounds composed of at least one hydrophobic moiety and at least one hydrophilic moiety. A basic property of surfactants and emulsifiers is that oriented absorption at the interfaces, as well as aggregation into micelles and the formation of lyotropic phases.

Surfactants that can be used within the framework of the present invention are selected from the group consisting of nonionic surfactants, anionic surfactants, amphoteric surfactants, zwitterionic surfactants, cationic surfactants, and mixtures thereof.

It is especially preferable, in the method according to the present invention, to use cosmetic agents (M1) that additionally contain at least one nonionic surfactant selected from the group consisting of: (i) alkylene oxide addition products onto alcohols having 8 to 30 carbon atoms, or carboxylic acids having 8 to 30 carbon atoms, containing in each case 2 to 30 mol ethylene oxide per mol alcohol or carboxylic acid; (ii) carboxylic acid esters of ethoxylated and/or propoxylated glycerol having 8 to 30 carbon atoms in the carboxylic acid chain and 1 to 30 mol ethylene oxide and/or propylene oxide per mol glycerol; and (iii) mixtures thereof.

Especially preferred methods according to the present invention are therefore characterized in that the cosmetic agents (M1) additionally contain at least one nonionic surfactant from the group consisting of carboxylic acid esters of ethoxylated and/or propoxylated glycols having 8 to 30 carbon atoms in the carboxylic acid chain and 1 to 30 mol ethylene oxide and/or propylene oxide per mol glycerol in a total amount of 0.1 to 10 wt %, preferably 0.5 to 5 wt %, in particular, 0.8 to 3 wt % relative to the total weight of the cosmetic agent (M1).

Furthermore, the pre-treatment agents (M1) may additionally contain at least one anionic surfactant. Preferred anionic surfactants are fatty acids, alkyl sulfates, alkyl ether sulfates, and ether carboxylic acids having 10 to 20 C atoms in the alkyl group and up to 16 glycol ether groups in the molecule. The anionic surfactants are used in a total amount of 0.1 to 45 wt %, preferably 1 to 30 wt %, in particular, 1 to 15 wt % relative to the total weight of the cosmetic agent (M1).

Moreover, it is also possible for the pre-treatment agents (M1) to additionally contain at least one zwitterionic and/or amphoteric surfactant. Preferred zwitterionic surfactants are betaines, N-alkyl-N,N-dimethylammonium glycinates, N-acyl aminopropyl-N,N-dimethyl ammonium glycinates, and 2-alkyl-3-carboxymethyl-3-hydroxyethyl imidazolines. An especially preferred zwitterionic surfactant is known under the INCI name Cocamidopropyl Betaine. Preferred amphoteric surfactants are N-alkylglycines, N-alkylpropionic acids, N-alkylaminobutyric acids, N-alkyliminodipropionic acids, N-hydroxyethyl-N-alkyl amidopropyl glycines, N-alkyl taurines, N-alkyl sarcosines, 2-alkylaminopropionic acids, and alkylaminoacetic acids. Particularly preferred amphoteric surfactants are N-cocoalkyl aminopropionate, cocoacylaminoethyl aminopropionate, and $C_{12}$-$C_{18}$ acyl sarcosine. The zwitterionic and/or amphoteric surfactants are used in a total amount of 0.1 to 45 wt %, preferably 1 to 30 wt %, in particular, 1 to 15 wt % relative to the total weight of the cosmetic agent (M1).

The pre-treatment agents (M1) may additionally contain at least one compound from the group consisting of the glycols. The term "glycols" is understood according to the present invention to mean compounds that have two hydroxyl groups.

Glycols that are suitable according to the present invention are selected from the group consisting of ethylene glycol, propylene glycol (1,2-propanediol), ethylene glycol monomethyl ether, trimethylene glycol, triethylene glycol, polyethylene glycol, neopentyl glycol, and mixtures thereof Especially preferred methods according to the present invention are characterized in that the cosmetic agents (M1) additionally contain at least one glycol from the group consisting of ethylene glycol, propylene glycol (1,2-propanediol), polyethylene glycol, and mixtures thereof in a total amount of 0.1 to 10 wt %, preferably 0.5 to 5 wt %, in particular, 0.8 to 3 wt % relative to the total weight of the cosmetic agent (M1).

The pre-treatment agents (M1) used within the framework of the method according to the present invention may also contain at least one alkalizing agent.

Organic alkalizing agents that can be used according to the present invention are preferably selected from alkanolamines of primary, secondary, or tertiary amines with a $C_2$-$C_6$ alkyl parent substance bearing at least one hydroxy group. Alkanolamines that are very especially preferred according to the present invention are selected from the group consisting of 2-aminoethan-1-ol (monoethanolamine), 2-amino-2-methylpropan-1-ol, 2-amino-2-methyl-propan-1,3-diol, and mixtures thereof. An especially preferred alkanolamine is monoethanolamine. Suitable alkaline amino acids are lysine, arginine, and ornithine. Inorganic alkalizing agents according to the present invention are preferably selected from the group consisting of sodium hydroxide, potassium hydroxide, calcium hydroxide, barium hydroxide, sodium phosphate, potassium phosphate, sodium silicate, potassium silicate, sodium carbonate, and potassium carbonate.

Methods that are especially preferred according to the present invention are characterized in that the cosmetic agent (M1) includes one or more alkalizing agents (from the group consisting of sodium hydroxide, potassium hydroxide, ammonia, monoethanolamine, and 2-amino-2-methylpropanol in a total amount of 0.5 to 8.0 wt %, preferably 0.1 to 6.0 wt %, in particular, 0.5 to 5.0 wt % relative to the total weight of the cosmetic agent (M1).

The pre-treatment agents (M1) used within the framework of the method according to the present invention generally have an alkaline pH value, in particular, between pH 7.0 and pH 14. These pH values are required in order to ensure opening of the outer cuticle layer and allow the oxidation dye precursors to penetrate into the hair.

Methods that are preferred according to the present invention are therefore characterized in that the cosmetic agent (M1) has a pH value of pH 7.0 to pH 14.0, preferably pH 8.8 to pH 11.0, preferably pH 9.0 to pH 10.8, in particular, pH 9.2 to pH 10.5. These pH values can preferably be adjusted with the use of the aforementioned alkalizing agents.

To enable clear and surprising emergence of the natural and multi-tonal dyeing result at the end of the method according to the present invention, the pre-treatment agent (M1) is preferably not independently capable of being used as a separate bleaching or lightening agent. For this, it is particularly advantageous when the cosmetic agents (M1) are free of oxidizing agents, in particular, free of hydrogen peroxide and/or persulfates.

The term "free of" signifies here, within the framework of the present invention, that the cosmetic agents (M1) do not contain any intentionally-added oxidizing agents. Nevertheless, traces of these oxidizing agents may be introduced into the cosmetic agents (M1) as contamination or an admixed substance accompanying other raw materials. More concretely, therefore, "free of" signifies that the cosmetic agents (M1) contain less than 1 wt %, preferably less than 0.5 wt %, preferably less than 0.25 wt %, further preferably less than 0.1 wt %, in particular, less than 0.01 wt % oxidizing agents, relative to the total weight of the cosmetic agent (M1).

Methods that are preferred according to the present invention are therefore characterized in that the cosmetic agent (M1) used in method step a) includes less than 1 wt %, preferably less than 0.5 wt %, preferably less than 0.25 wt %, further preferably less than 0.1 wt %, in particular, less than 0.01 wt % peroxo compounds relative to the total weight of the cosmetic agent (M1). Peroxo compounds are understood within the framework of the present invention to mean compounds containing at least one peroxide anion $O_2^{2-}$ or at least one peroxy group —O—O—.

Methods that are especially preferred according to the present invention are characterized in that the cosmetic agent (M1) used in method step a) includes less than 1 wt %, preferably less than 0.5 wt %, preferably less than 0.25 wt %, further preferably less than 0.1 wt %, in particular, less than 0.01 wt % hydrogen peroxide relative to the total weight of the cosmetic agent (M1).

In method step c) of the method according to the present invention, a cosmetic agent (M2) is applied onto the keratinous fibers, which are still being exposed to the agent (M1). This cosmetic agent (M2), which is hereinafter also designated a coloring agent, includes at least one oxidation dye precursor (M2-1) and at least one oxidizing agent (M2-2).

Preferred cosmetic agents (M2) contain at least one oxidation dye precursor of the developer and/or coupler type. Corresponding methods according to the present invention in which the cosmetic agent (M2) includes one or more oxidation dye precursors of the developer type as the oxidation dye precursor are preferred according to the present invention.

It has been shown that the use of certain oxidation dye precursors (M2-1) of the developer type in certain quantities in the coloring agents (M2) is well suited for generating especially vivid and wash-, abrasion-, sweat-, and UV-fast multi-tonal colorations.

It is therefore preferable according to the present invention for the at least one oxidation dye precursor (M2-1) of the developer type to be selected from the group consisting of 4,5-diamino-1-(2-hydroxyethyl)pyrazol, 2,4,5,6-tetraaminopyrimi dine, 4-hydroxy-2,5,6-triaminopyrimidine, 2-hydroxy-4,5,6-triaminopyrimidine, 2,3-diamino-6,7-dihydro-1H, 5H-pyrazolo [1,2-a]pyrazol-1-one, p-phenylenediamine, p-toluylendiamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, physiologically acceptable salts thereof, and mixtures thereof.

Obtaining natural colorations typically requires the use of a plurality of oxidation dye precursors (M2-1) of the developer type. Preferred cosmetic agents (M2) are therefore characterized in that the at least one oxidation dye precursor (M2-1) of the developer type is selected from at least one of the following combinations: p-toluylendiamine/2-(2-hydroxyethyl)-p-phenylenediamine; p-toluylendiamine/2-methoxymethyl-p-phenylenediamine; p-toluylendiamine/N,N-bis-(2-hydroxyethyl)-p-phenylenediamine; p-toluylendiamine/2-methoxymethyl-p-phenylenediamine; p-toluylendiamine/N-(4-amino-3-methylphenyl)-N-[3-(1h-imidazol-1-yl)propyl]amine; p-toluylendiamine/bis-(2-hydroxy-5-aminophenyl)methane; p-toluylendiamine/4-amino-3-methylphenol; p-toluyl endiamine/4,5-diamino-1-(2-hydroxyethyl)pyrazole; p-toluylendiamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis-(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methylphenyl)-N-[3-(1h-imidazol-1-yl)propyl]amine; 2-(2-hydroxyethyl)-p-phenylenediamine/bis-(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis-(2-hydroxyethyl)-p-phenylenediamine; 2-methoxymethyl-p-phenylenediamine/2-methoxymethyl-p-phenylenediamine;

2-methoxymethyl-p-phenylendiamin/N-(4-amino-3-methylphenyl)-N-[3-(1H-imidazol-1-yl)-propyl]amine; /bis-(2-hydroxy-5-aminophenyl)methane; 2-methoxymethyl-p-phenylenediamine/4-amino-3-methylphenol; 2-methoxymethyl-p-phenylendiamine/4,5-diamino-1-(2-hydroxyethyl)pyrazole; 2-methoxymethyl-p-phenylenediamine/2,4,5,6-tetraaminopyrimidine, and/or 4-and amino-3-methyl-pheno1/4,5-diamino-1-(2-hydroxyethyl)pyrazole, and/or physiologically acceptable salts thereof.

According to an especially preferred embodiment of the first subject matter of the present invention, the at least one oxidation dye precursor (M2-1) of the developer type is selected from the group consisting of p-toluenediamine, 4-amino-3-methylphenol, 4,5-diamino-1-(2-hydroxyethyl)pyrazole, 2,4,5,6-tetraaminopyrimidine, and/or physiologically acceptable salts thereof and mixtures thereof, and is contained in a total amount of 0.0005 to 3.0 wt %, preferably 0.001 to 2.75 wt %, preferably 0.0025 to 2.5 wt %, in particular, 0.005 to 2.0 wt % relative to the total weight of the cosmetic agent (M2). It has been shown that the use of these specific oxidation dye precursors (M2-1) of the developer type in the aforementioned quantities in the coloring agents (M2) leads to especially vivid and wash-, abrasion-, sweat-, and UV-fast multi-tonal colorations.

The coloring agent (M2) may contain at least one oxidation dye precursor (M2-1) of the coupler type as an additional component. Oxidation dye precursors of the coupler type do not produce a significant coloration within the framework of the oxidative dyeing, but rather require the presence of oxidation dye precursors of the developer type in order to produce adequate coloration. Oxidation dye precursors of the coupler type in the sense of the present invention allow at least one substitution of a chemical residue of the coupler by the oxidized form of the developer component. This forms a covalent bond between the coupler and developer components. Within the framework of the present invention, it is preferable when the at least one oxidation dye precursor (M2-1) of the coupler type is selected from the group consisting of m-aminophenol and derivatives thereof, o-aminophenol and derivatives thereof, o-diaminobenzene and derivatives thereof, di- and trihydroxybenzene derivatives, pyridine derivatives, naphthalene derivatives, morpholine derivatives, quinoxaline derivatives, pyrazole derivatives, indole derivatives, pyrimidine derivatives, methylenedioxybenzene derivatives, and/or physiologically acceptable salts thereof and mixtures thereof.

Preferred methods according to the present invention are therefore characterized in that the at least one oxidation dye precursor (M2-1) of the coupler type is selected from the group consisting of resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, 1-naphthol, and/or physiologically acceptable salts thereof and mixtures thereof, in a total amount of 0.001 to 2.0 wt %, preferably 0.0025 to 1.75 wt %, preferably 0.0025 to 1.5 wt %, in particular, 0.005 to 1.25 wt %, relative to the total weight of the cosmetic agent (M2). The aforementioned coupler components in the specified quantity ranges, in combination with the aforementioned developer components in the coloring agent (M2), lead to especially intense and stable multi-tonal dyeing results.

Particularly appealing multi-tonal colorations are obtained when the cosmetic agent (M2) includes the at least one oxidation dye precursor (M2-1) in a total amount of 0.01 to 4.0 wt %, preferably 0.008 to 3.75 wt %, preferably 0.005 to 3.5 wt %, in particular, 0.005 to 3.2 wt %, relative to the total weight of the cosmetic agent (M2). The aforementioned quantities of the at least one oxidation dye precursor (M2-1) lead to multi-tonal colorations that have especially intense and brilliant colors as well as a high resistance to environmental influences such as hair washing, UV light, sweat, and friction or abrasion.

The coloring agent (M2) may additionally contain direct dyes, in order to ensure a balanced shading in the multi-tonal colorations. According to a preferred embodiment of the first subject matter of the present invention, the cosmetic agent (M2) additionally includes at least one direct dye from the group consisting of anionic direct dyes, cationic direct dyes, nonionic direct dyes, and mixtures thereof.

Suitable and preferred direct dyes have already been described in detail in connection with the pre-treatment agent (M1). The corresponding compounds may also be used in the coloring agents (M2). It has, however, been shown that the use of certain direct dyes in certain quantities in the coloring agents (M2) is especially suitable, because in this case an especially balanced shading in the multi-tonal colorations can be ensured.

Cosmetic agents (M2) that are especially preferably used in one embodiment of the method according to the present invention therefore additionally contain at least one direct dye selected from group consisting of 2-amino-6-chloro-4-nitrophenol, HC Blue 12, HC Yellow 2, HC Violet 14D, and/or physiologically acceptable salts and mixtures thereof Methods according to the present invention within the framework of this embodiment are characterized in that the cosmetic agent (M2) includes the at least one direct dye in a total amount of 0.00005 to 5.0 wt %, preferably 0.0001 to 4.0 wt %, preferably 0.0005 to 3.0 wt %, further preferably 0.0001 to 2.0 wt %, in particular, 0.0005 to 1.5 wt %, relative to the total weight of the cosmetic agent (M2).

When the coloring agent (M2) includes a direct dye, then it is preferable within the framework of the present invention when the pre-treatment agent (M1) includes a greater total amount of direct dyes (M1-1) than does the cosmetic agent (M2). This leads to especially intense and vivid multi-tonal colorations, which moreover exhibit high resistance to environmental influences such as hair washing, sweat, UV light, or friction/abrasion.

It is therefore preferable, in this context, when the ratio of the total amount of all of the direct dyes (M1-1) in the cosmetic agent (m1) to the total amount of all of the direct dyes in the cosmetic agent (M2) has a value of 1:5 to 1:1, preferably 150:1 to 250:1, preferably 450:1 to 550:1, further preferably 900:1 to 1,100:1, still further preferably 2,500:1 to 3,500:1, in particular, 5,500:1 to 6,500:1.

Furthermore, in this context, variation in the shades of the multi-tonal coloration can be achieved through appropriate selection of the direct dyes used in the cosmetic agents (M1) and (M2). For a very natural-looking multi-tonal coloration with smooth transitions, therefore, preferred methods according to the present invention are those in which the cosmetic agents (M1) and (M2) contain identical direct dyes.

If, however, stronger contrasts that make themselves apparent in a more brilliant multi-tonal appearance of the coloration are desired, methods according to the present invention in which the cosmetic agents (M1) and (M2) contain different direct dyes have proven advantageous. The coloring agents (M2) may moreover contain additional active agents, auxiliary substances, and additives to improve the coloring capacity and to establish further desired properties of the cosmetic agents (M2).

Preferably according to the present invention, therefore, the cosmetic agent (M2) additionally includes at least one additional compound selected from the group consisting of (i) thickening agents, (ii) linear or branched saturated or unsaturated alcohols having 8 to 20 carbon atoms, (iii) surfactants, (iv) alkalizing agents, and (v) mixtures thereof It has proven advantageous when the cosmetic agents (M2) also contain at least one thickening agent. There are no restrictions in principle regarding these thickening agents. Suitable thickening agents are those compounds that were mentioned in connection with the pre-treatment agent (M2), which can also be used to thicken the coloring agent (M2). In addition, the following organic and inorganic thickening agents may also be used.

Suitable thickening agents are anionic synthetic polymers, cationic synthetic polymers, and nonionic synthetic polymers, such as polyvinyl alcohol or polyvinyl pyrrolidone.

The cosmetic agents (M2) used in the method according to the present invention may also contain, as a thickening agent, zwitterionic polymers selected from the group consisting of:

copolymers of dimethyldiallylammonium salts and acrylic acid, e.g. Polyquaternium-22;
copolymers of dimethyldiallylammonium salts and methacrylic acid;
copolymers of N,N,N-trimethyl-3-[(2-methyl-1-oxo-2-propen-1-yl)amino]-1-propanaminium salts and acrylic acid;
copolymers of N,N,N-trimethyl-3-[(2-methyl-1-oxo-2-propen-1-yl)amino]-1-propanaminium salts and methacrylic acid;
copolymers of N,N,N-Trimethyl-2-[(2-methyl-1-oxo-2-propen-1-yl)amino]-1-ethanaminium salts and acrylic acid;
copolymers of N,N,N-Trimethyl-2-[(2-methyl-1-oxo-2-propen-1-yl)amino]-1-ethanaminium salts and methacrylic acid;
copolymers of N,N,N-trimethyl-3-[(2-methyl-1-oxo-2-propen-1-yl)amino]-1-propanaminium salts, acrylic acid, and acrylamide, e.g. Polyquaternium-53;
copolymers of N,N,N-trimethyl-3-[(2-methyl-1-oxo-2-propen-1-yl)amino]-1-propanaminium salts, methacrylic acid, and acrylamide;
copolymers of 1-ethenyl-3-methyl-1H-imidazolium salts, 1-ethenyl-1H-imidazole, 1-ethenyl-2-pyrrolidinone, and methacrylic acid, e.g. Polyquaternium-86; and
copolymers of 1-ethenyl-3-methyl-1H-imidazolium salts, 1-ethenyl-1H-imidazole, 1-ethenyl-2-pyrrolidinone, and acrylic acid.

Mixtures of the aforesaid preferred zwitterionic polymers may also be used to thicken the cosmetic agents (M2).

The coloring agents (M2) used according to the present invention in method step c) may contain linear or branched saturated or unsaturated alcohols having 8 to 20 carbon atoms. It has been found that the additional presence of these longer-chain alcohols can still further improve the multi-tonal dyeing result of the method according to the present invention. It is therefore preferable when the cosmetic agents (M2) used in the method according to the present invention additionally contain one or more alcohols from the group consisting of arachyl alcohol (eicosan-1-ol), gadoleyl alcohol ((9Z)-eicos-9-en-1-ol), arachidonyl alcohol ((5Z, 8Z, 11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E) -docosen-1-ol).

Especially suitable cosmetic agents (M2) contain one or more longer-chained alcohols of the aforementioned group in a total amount of 1.0 to 10.0 wt %, preferably 1.4 to 8.5 wt %, preferably 1.8 to 8.0 wt %, in particular, 2.0 to 7.0 wt % relative to the total weight of the cosmetic agent (M2).

Preferably, the coloring agents (M2) are provided as a liquid preparation and a surface-active substance is therefore additionally added to these means, wherein such surface-active substances are called surfactants or emulsifiers, depending on the area of use: They are preferably selected from anionic, cationic, zwitterionic, amphoteric, and nonionic surfactants and emulsifiers.

Within the framework of this embodiment, it may be provided that the anionic surfactant is selected from the group consisting of alkyl sulfates and alkyl polyglycol ether sulfates of the formula $R^2$—$O(CH_2$—$CH_2O)_x$—$OSO_3H$ in which $R^2$ is a linear alkyl group having 8 to 30 carbon atoms and x=0 or 1 to 12, salts of linear and branched carboxylic acids having 8 to 30 carbon atoms, ether carboxylic acids of the formula $R^3$—O—$(CH_2$—$CH_2O)_x$—$CH_2$—$COOH$ in which $R^3$ is a linear alkyl group having 8 to 30 C atoms and x=0 or 1 to 16, and mixtures thereof. The anionic surfactants are preferably used in a total amount of 0.1 to 45 wt %, preferably 1 to 30 wt %, in particular, 1 to 15 wt % relative to the total amount of the cosmetic agent (M2).

In this context, it may furthermore be provided according to the present invention that the nonionic surfactant is selected from the group consisting of ethoxylated alcohols and carboxylic acids having 8 to 13 carbon atoms and 2 to 30 ethylene oxide units, addition products of 5 to 60 mol ethylene oxide to castor oil and hydrogenated castor oil, alkyl polyglucosides of the formula $R^1O$-$[G]_p$ in which $R^1$ designates an alkyl and/or alkyl residue having 4 to 22 carbon atoms, G designates a sugar residue having 5 or 6 carbon atoms, and p designates numbers 1 to 10, monoethanolamides of carboxylic acids having 8 to 30 carbon atoms, and mixtures thereof.

It may, moreover, also be provided within the framework of this embodiment that the amphoteric surfactant is selected from the group consisting of amphoacetates having carboxylic acid esters having 8 to 30 carbon atoms, N-alkylglycines, N-alkylpropionic acids, N-alkylamidobutyric acids, N-alkyliminodipropionic acids, N-hydroxyethyl N-alkylamidopropylglycines, N-alkyltaurines, N-alkylsarcosines, 2-alkylaminopropionic acids, alkylaminoacetic acids, and mixtures thereof.

Within the framework of this embodiment, it may also be provided that the zwitterionic surfactant is selected from the group consisting of betaines, N-alkyl-N,N-diemthylammonium glycinates, N-acyl-amidopropyl-N,N-dimethylammonium glycinates, 2-alkyl-3-carboxymethyl-3-hydroxyethyl imidazolines, and mixtures thereof The nonionic and/or zwitterionic and/or amphoteric surfactants are preferably used in a total amount of 0.1 to 45 wt %, preferably 1 to 30 wt %, in particular, 1 to 15 wt % relative to the total amount of the cosmetic agent (M2).

The cosmetic agent (M2) may also contain at least one alkalizing agent. Suitable alkalizing agents and the usable total amounts thereof have already been mentioned in connection with the pre-treatment agent (M1). To ensure opening of the outer cuticle layer and enable the oxidation dye precursor to penetrate into the hair, it is necessary to set an alkaline pH value with the use of the at least one alkalizing agent.

Methods that are preferred according to the present invention are therefore characterized in that the cosmetic agent (M2) has a pH value of pH 7.0 to pH 14.0, preferably pH 8.8 to pH 11.0, preferably pH 9.0 to pH 10.8, in particular, pH 9.2 to pH 10.5.

In order to achieve vivid multi-tonal coloration, it is advantageous when sequential application of the cosmetic agents (M1) and (M2) does not bring about excessive fluctuations in pH value, because this may produce an only insufficient penetration into the keratinous fibers and thus an adversely affected dyeing result. Preferred methods according to the present invention are therefore those in which the cosmetic agent (M1) and the cosmetic agent (M2) have identical pH values.

The oxidation dye precursors (developer and coupler) are themselves not colored. The actual dyes are formed first in the course of use through the context of the oxidation dye precursors with an oxidizing agent (preferably hydrogen peroxide). In a chemical reaction, the developers (for example, p-phenylenediamine derivatives or p-aminophenol derivatives) used as the oxidation dye precursors are first oxidatively converted by hydrogen peroxide into a reactive intermediate, also known as quinonimine or quinonediimine, which then reacts in an oxidative coupling reaction with the couplers to make the respective dye.

The cosmetic agents (M2) therefore additionally contain one or more oxidizing agents (M2-2). Possible oxidizing agents include persulfates, peroxodisulfates, chlorites, hypochlorites, and, in particular, hydrogen peroxide and/or a solid addition product thereof to organic or inorganic compounds.

Methods that are preferred according to the present invention are therefore characterized in that the cosmetic agent (M2) includes at least one oxidizing agent (M2-2) from the group consisting of persulfates, peroxodisulfates, chlorites, hypochlorites, hydrogen peroxide, and solid addition products thereof to urea, melamine, polyvinyl pyrrolidone, and sodium borate, preferably hydrogen peroxide, in a total amount of 0.5 to 10 wt %, preferably 1.0 to 10 wt %, in particular, 1.5 to 10 wt %, relative to the total weight of the cosmetic agent (M2). If hydrogen peroxide and solid addition products thereof are used as the oxidizing agent, the aforementioned total amount refers to 100% $H_2O_2$.

In another preferred embodiment, the cosmetic agent (M2) is an agent for dyeing and optionally simultaneously brightening keratinous fibers, which includes hydrogen peroxide in a total amount of 0.5 to 15 wt %, preferably 1 to 12.5 wt %, preferably 1.5 to 10 wt %, in particular, 1.5 to 6.5 wt % relative to the total weight of the cosmetic agent (M2). The aforementioned total amount of hydrogen peroxide is relative here to 100% $H_2O_2$.

To achieve a more powerful brightening and bleaching effect, the cosmetic agent (M2) may furthermore contain at least one peroxo salt. Suitable peroxo salts are inorganic peroxo compounds, preferably selected from the group consisting of ammonium peroxodisulfate, alkali metal peroxodisulfates, ammonium peroxomonosulfate, alkali metal peroxomonosulfates, alkali metal peroxodiphosphates, alkaline earth metal peroxides, and mixtures thereof. Especially preferred are peroxodisulfates, in particular, ammonium peroxodisulfate, potassium peroxodisulfate, and sodium peroxodisulfate.

The aforementioned peroxo salts are contained in a total amount of 0.5 to 20 wt %, preferably 1.0 to 12.5 wt %, preferably 2.5 to 10 wt %, in particular, 3.0 to 6.0 wt % relative to the total weight of the cosmetic agent (M2).

In order to prevent a premature, undesired reaction of the oxidation dye precursors due to the oxidizing agent, oxidation dye precursors and oxidation agents should be manufactured separately from one another and only brought into contact immediately before use. Usually, oxidative coloring agents are therefore offered in the form of a "kit" (multi-component packaging unit) composed of two components, wherein the first component includes the oxidation dye precursors and optionally direct dyes as well as an alkalizing agent (for example, ammonia) and the second component includes the oxidizing agent.

In another embodiment of the present invention, therefore, the cosmetic agents (M2) are preferably characterized by being produced immediately before use by mixing at least two preparations, wherein the at least two preparations are provided in at least two separately-manufactured containers, and wherein one contain includes a coloring agent (M2a) containing at least one oxidation dye precursor in a cosmetic support, and another container includes an oxidizing agent preparation (M2b) containing at least one oxidizing agent.

The coloring agent (M2a) preferably here includes the oxidation dye precursors of the developer type and/or coupler type that were mentioned in connection with the cosmetic agent (M2), optionally at least one direct dye, and optionally at least one active agent, auxiliary substance, or additive mentioned that was mentioned in connection with the cosmetic agent (M2). The oxidizing agent preparation (M2b) preferably includes an oxidizing agent in the form of hydrogen peroxide and/or a solid addition product thereof to organic or inorganic compounds, such as urea, melamine, and sodium borate.

Such oxidizing agent preparations (M2b) are preferably aqueous, flowable oxidizing agent preparations. Then, preferred preparations (M2b) are characterized in that the flowable oxidizing agent preparation (M2b) includes 40 to 90 wt %, preferably 50 to 90 wt %, preferably 55 to 89 wt %, further preferably 60 to 87 wt %, in particular, 65 to 85 wt % water relative to the total weight of the oxidizing agent preparation (M2b).

Preferably, the total amount of oxidizing agent, in particular, hydrogen peroxide in the oxidizing agent preparation (M2b) is 0.5 to 12 wt %, preferably 2.0 to 10 wt %, in particular, 1.5 to 6.0 wt % relative to the total weight of the oxidizing agent preparation (M2b). If hydrogen peroxide and solid addition products thereof are used as the oxidizing agent, the aforementioned total amount refers to 100% $H_2O_2$.

According to the present invention, the oxidizing agent preparation (M2b) may also be applied to the hair together with a catalyst that activates the oxidation of the dye precursors. Examples of such catalysts include certain enzymes, iodide, quinones, or metal ions.

It has proven advantageous when the oxidizing agent preparations (M2b) additionally contain at least one stabilizer or complexing agent, in order to stabilize the oxidizing agent, in particular, the hydrogen peroxide. Especially preferred stabilizers are, in particular, EDTA and EDDS as well as phosphonates, in particular, 1-hydroxyethane-1,1-diphosphonate (HEDP) and/or ethylenediamine tetramethylenephosphonate (EDTMP) and/or diethylenetriamine pentamethylenephosphonate (DTPMP) or sodium salts thereof While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for oxidatively dyeing keratinous fibers to achieve a multi-tonal color effect, wherein the method comprises the following method steps in the specified order:
   a) applying a cosmetic agent (M1) to the keratinous fibers, wherein the application of the cosmetic agent (M1) is varied and uneven over individual regions of the keratinous fibers to achieve the multi-tonal color effect,
   b) allowing the agent (M1) to act on the keratinous fibers for a period of time of 30 seconds to 40 minutes,
   c) applying a cosmetic agent (M2) to the keratinous fibers exposed to the cosmetic agent (M1),
   d) allowing the cosmetic agents (M1) and (M2) to act on the keratinous fibers for a period of time of 1 to 70 minutes, and
   e) rinsing out the cosmetic agents (M1) and (M2),
wherein
   the cosmetic agent (M1) includes
   at least one direct dye (M1-1),
   at least one thickening agent (M1-2), and
   no oxidation dye precursors (M1-3); and
   the cosmetic agent (M2) includes
   at least one oxidation dye precursor (M2-1), and
   at least one oxidizing agent (M2-2).

2. The method according to claim 1, wherein cosmetic agent (M1) is allowed to act on the keratinous fibers in the method step b) for a duration of 30 seconds to 30 minutes.

3. The method according to claim 1, wherein cosmetic agent (M1) is applied only to individual small strands in method step a).

4. The method according to claim 1, wherein cosmetic agents (M1) and (M2) are allowed to act for a duration of 1 to 60 minutes in method step d).

5. The method according to claim 1, wherein the at least one direct dye (M1-1) is selected from the group consisting of 2-amino-6-chloro-4-nitrophenol, HC Blue 12, HC Yellow 2, HC Violet 14 D, and/or physiologically acceptable salts thereof and mixtures thereof.

6. The method according to claim 1, wherein cosmetic agent (M1) includes the at least one direct dye (M1-1) in a total amount of 0.0001 to 5.5 wt % relative to the total weight of the cosmetic agent (M1).

7. The method according to claim 1, wherein the at least one thickening agent (M1-2) is one or more selected from the group consisting of: celluloses; cellulosic derivatives; xanthan; crosslinked homopolymers or copolymers of acrylic acid, methacrylic acid, and salts thereof; crosslinked copolymers of ethoxylated alkyl esters of methacrylic acid, sulfonated acrylamides, and salts thereof; crosslinked copolymers of methacrylic acid, acrylamides, and sulfonated acrylamides, and salts thereof.

8. The method according to claim 1, wherein the cosmetic agent (M1) includes the at least one thickening agent (M1-2) in a total amount of 0.1 to 5.0 wt % relative to the total weight of the cosmetic agent (M1).

9. The method according to claim 1, wherein the cosmetic agent (M1) used in method step a) includes less than 1.0 wt % oxidation dye precursors relative to the total weight of the cosmetic agent (M1).

10. The method according to claim 1, wherein cosmetic agent (M1) has a dynamic viscosity of 5,000 to 90,000 mPa·s as measured with a Brookfield RDV II+, spindle nr. 4, 4 rpm, 20° C.

11. The method according to claim 1, wherein cosmetic agent (M1) has a pH value of 7.0 to 14.0.

12. The method according to claim 1, wherein cosmetic agent (M2) includes at least one oxidation dye precursor of the developer type and/or coupler type as the oxidation dye precursor (M2-1).

13. The method according to claim 1, wherein cosmetic agent (M2) includes the at least one oxidation dye precursor (M2-1) in a total amount of 0.01 to 4.0 wt % relative to the total weight of the cosmetic agent (M2).

14. The method according to claim 1, wherein the cosmetic agent (M1) and the cosmetic agent (M2) have identical pH values.

15. The method according to claim 1, wherein cosmetic agent (M2) includes at least one oxidizing agent (M2-2) selected from the group consisting of persulfates, peroxodisulfates, chlorites, hypochlorites, hydrogen peroxide and solid addition products thereof, urea, melamine, polyvinyl pyrrolidone, and sodium borate in a total amount of 0.5 to 10 wt % relative to the total weight of the cosmetic agent (M2).

16. The method according to claim 1, wherein the step b) of allowing the cosmetic agent (M1) to act on the keratinous fibers at a temperature of 30° C. to 120° C.

17. The method according to claim 16, wherein the step b) of allowing the cosmetic agent (M1) to act on the keratinous fibers at a temperature of 40° C. to 120° C.

* * * * *